(12) United States Patent
Kleinmann et al.

(10) Patent No.: US 11,730,839 B2
(45) Date of Patent: Aug. 22, 2023

(54) SURFACE DECONTAMINATION DEVICE AND OPERATING METHOD

(71) Applicant: Metall + Plastic GmbH, Radolfzell (DE)

(72) Inventors: Stefan Kleinmann, Radolfzell (DE); Thomas Kassner, Radolfzell (DE)

(73) Assignee: METALL + PLASTIC GMBH, Radolfzell (DE)

( * ) Notice: Subject to any disclaimer, the term of this patent is extended or adjusted under 35 U.S.C. 154(b) by 530 days.

(21) Appl. No.: 16/761,978

(22) PCT Filed: Nov. 5, 2018

(86) PCT No.: PCT/EP2018/080156
§ 371 (c)(1),
(2) Date: May 6, 2020

(87) PCT Pub. No.: WO2019/091910
PCT Pub. Date: May 16, 2019

(65) Prior Publication Data
US 2021/0187139 A1 Jun. 24, 2021

(30) Foreign Application Priority Data
Nov. 7, 2017 (EP) .................... 17200414

(51) Int. Cl.
*A61L 2/08* (2006.01)
*B65B 55/08* (2006.01)
*A61L 2/24* (2006.01)

(52) U.S. Cl.
CPC .............. *A61L 2/087* (2013.01); *B65B 55/08* (2013.01); *A61L 2/24* (2013.01); *A61L 2202/122* (2013.01);
(Continued)

(58) Field of Classification Search
CPC ...... A61L 2/087; A61L 2/24; A61L 2202/122; A61L 2202/14; A61L 2202/23; A61L 2202/121; B65B 55/08
See application file for complete search history.

(56) References Cited

U.S. PATENT DOCUMENTS

| 4,990,047 A * | 2/1991 | Wagner | H01L 21/67167 |
| | | | 414/217 |
| 5,135,122 A * | 8/1992 | Gross | A23L 3/0055 |
| | | | 34/259 |

(Continued)

FOREIGN PATENT DOCUMENTS

| CN | 101193660 A | 6/2008 |
| CN | 104335290 A | 2/2015 |

(Continued)

OTHER PUBLICATIONS

Metall + Plastic Gmbh, "E-Beam Tunnel", Jan. 10, 2017 Jul. 2016 (Jul. 17, 2016), Retrieved from the Internet: https://www.metall-plastic.com/de-de/e-beam-tunnel, [retrieved on May 3, 2018], XP055472115, pp. 1, 3; figure 1.

(Continued)

*Primary Examiner* — Regina M Yoo
(74) *Attorney, Agent, or Firm* — Bachman & LaPointe, P.C.

(57) ABSTRACT

A surface decontamination device (1) for decontaminating outer packagings (2) which contain pre-sterilised consumer goods and have a circumferential collar (3) prior to transfer into an insulator includes a conveyor for conveying the outer packagings (2) in a conveying direction (F) along a conveying path from an inlet side to an outlet side of the device (1). The conveying path passes through a decontamination chamber (5) between the inlet side and outlet side. An irradiation source (6) is associated with the chamber (5) for irradiating the outer packagings (2) conveyed through the (Continued)

chamber (5). The conveying path passes through at least one lock chamber (8) arranged between the inlet side and outlet side, adjacent to the chamber (5) and having an inlet and an outlet, the inlet and outlet being able to be opened and closed by a closer. The conveyor includes a suspended transport unit (7) in the chamber (5) for suspended transport of the outer packagings (2) on the circumferential collar (3) thereof, wherein a lifting unit (11, 15) for automatic, vertical adjustment of the outer packagings (2) relative to the suspended transport unit (7) is arranged in the lock chamber (8, 14).

18 Claims, 1 Drawing Sheet

(52) U.S. Cl.
CPC ....... *A61L 2202/14* (2013.01); *A61L 2202/23* (2013.01)

(56) References Cited

U.S. PATENT DOCUMENTS

| | | | | | |
|---|---|---|---|---|---|
| 5,223,001 | A | * | 6/1993 | Saeki | H01L 21/67751 414/217 |
| 5,599,398 | A | * | 2/1997 | Lenglen | B08B 3/12 134/32 |
| 5,766,382 | A | * | 6/1998 | Hertzog | C21D 9/0056 148/656 |
| 5,964,043 | A | * | 10/1999 | Oughton | F26B 5/06 34/92 |
| 6,106,748 | A | * | 8/2000 | Sisbarro | B29C 33/444 264/39 |
| 6,129,879 | A | * | 10/2000 | Bersted | B29C 48/79 8/531 |
| 6,279,505 | B1 | * | 8/2001 | Plester | C23C 14/10 118/723 VE |
| 6,297,479 | B1 | * | 10/2001 | Wefers | A23L 19/03 34/264 |
| 7,658,017 | B1 | * | 2/2010 | Laviolette | F26B 5/042 34/403 |
| 2002/0017033 | A1 | * | 2/2002 | Wefers | F26B 5/048 34/264 |
| 2004/0231184 | A1 | * | 11/2004 | Wefers | A23L 19/01 34/380 |
| 2005/0123435 | A1 | * | 6/2005 | Cutler | B65B 55/02 422/1 |
| 2005/0186716 | A1 | * | 8/2005 | Kasumi | H01L 21/67751 438/149 |
| 2007/0272150 | A1 | * | 11/2007 | Swoboda | F26B 21/14 118/642 |
| 2008/0193341 | A1 | | 8/2008 | Fontcuberta et al. | |
| 2008/0314730 | A1 | * | 12/2008 | Pringle | C10G 1/04 204/157.6 |
| 2010/0032055 | A1 | * | 2/2010 | Sangi | A61L 9/16 141/168 |
| 2011/0016829 | A1 | * | 1/2011 | Drenguis | B65B 55/08 53/167 |
| 2011/0283661 | A1 | * | 11/2011 | Miller | A61L 2/10 53/425 |
| 2013/0109189 | A1 | * | 5/2013 | Cho | H01L 31/18 156/345.31 |
| 2019/0169800 | A1 | * | 6/2019 | Hardacre | D21F 5/167 |

FOREIGN PATENT DOCUMENTS

| | | |
|---|---|---|
| CN | 206013237 U | 3/2017 |
| EP | 1051197 A2 | 11/2000 |
| EP | 2854138 A1 | 4/2015 |
| WO | 2008055375 A1 | 5/2008 |
| WO | 2012147007 A1 | 11/2012 |

OTHER PUBLICATIONS

International search report for patent application No. PCT/EP2018/080156 dated Feb. 19, 2019.

* cited by examiner

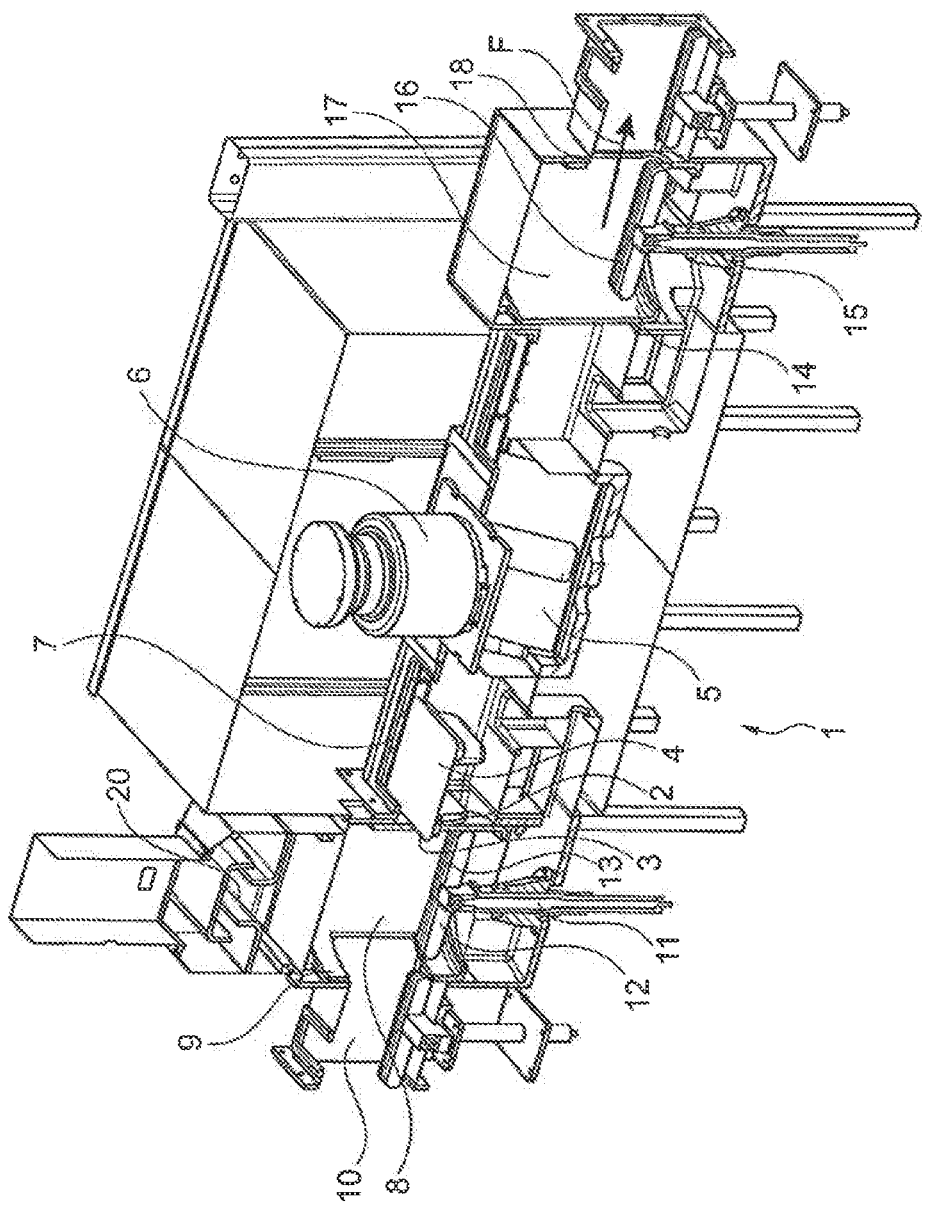

SURFACE DECONTAMINATION DEVICE AND OPERATING METHOD

BACKGROUND OF THE INVENTION

The invention relates to a surface decontamination device, in particular for pharmaceutical applications, for decontaminating outer packaging which contains pre-sterilized consumer goods, such as prefilled syringes, packaging of medicine, etc., and which has a circumferential collar prior to the transfer into an isolator, in which the pre-sterilized consumer goods are processed, in particular filled with a pharmaceutical ingredient or the like. The consumer goods can be unpacked from the outer packaging either directly in the isolator, in particular a manipulator chamber of the isolator, or in a clean-room unpacking chamber which is disposed upstream of the isolator and which is preferably realized as a lock. The consumer goods can be unpacked either manually, in particular via gloves which reach into an unpacking chamber or clean room, or automatically by means of a corresponding unpacking device, a film sealed on the circumferential collar of the outer packaging being preferably removed and/or opened to open the outer packaging. In addition or as an alternative to the aforementioned circumferential collar having a film sealed thereon, the circumferential collar of the outer packaging can be realized by an, in particular circumferential, annular shoulder in the circumferential wall of the outer packaging, starting from which the circumferential wall extends upwards towards an upper side of the outer packaging, in particular a lid film, and, on the opposite side, downwards towards a bottom side of the outer packaging. The surface decontamination device realized according to the idea of the invention is preferably realized as a transfer device. The surface decontamination device comprises conveying means for conveying the outer packaging in a conveying direction along a conveying path from an inlet side of the device to an outlet side of the device which is preferably either directly followed by the isolator or by a facultative unpacking chamber having a subsequent isolator. The conveying path on which the outer packaging is conveyed in the surface decontamination device passes through a decontamination chamber (irradiation chamber) which is disposed between the inlet side and the outlet side and which is assigned a radiation source (radiation emitter), in particular an electrode beam source, for irradiating the outer packaging which can be or is conveyed through the decontamination chamber, the conveying means comprising a suspension transport device disposed in the decontamination chamber for the suspended transport of the outer packaging by its circumferential collar, the suspension transport device being preferably realized so as to clamp the circumferential collar, in particular on two opposite sides, during the transport. Furthermore, the conveying path passes through at least one lock chamber which is disposed between the inlet side and the outlet side and which is adjacent to the decontamination chamber, in particular directly adjoining said decontamination chamber, and which has an inlet and an outlet, the inlet and the outlet of the lock chamber being openable and or closable by means of closing means, in particular in an alternating manner, in order to prevent radiation from escaping from the decontamination chamber into an area (disposed upstream or downstream of the lock chamber in the conveying direction depending on the disposition of the lock chamber).

Furthermore, the invention relates to a system having a surface decontamination device according to the invention which is disposed downstream of an isolator along the conveying path.

The invention also relates to a method for operating a surface decontamination device according to the invention and/or a system according to the invention all as disclosed herein.

Due to the increased use of pre-sterilized, in particular nested, consumer goods, such as prefilled syringes for vaccines or insulin, decontamination of the outer packaging containing the consumer goods by electron irradiation is increasingly used as a transfer technology for transferring the consumer goods into an isolator, in particular because this technology allows for a continuous supply into the isolator.

In order to avoid any risk to the users related to the radiation emitted into the decontamination chamber to decontaminate the outer surface of the outer packaging, different technologies are known. According to a proven technology, the outer packaging is transferred from a first height level to a second height level which is spaced apart by a multiple of a vertical dimension of the outer packaging along the vertical by means of a paternoster system, the decontamination chamber comprising the radiation source being located on the second height level, the outer packaging being displaced back to the first height level after passing through the decontamination chamber. A labyrinth system which reliably prevents radiation from escaping is thus realized, because most of the radiation energy is absorbed after a two-time impact or reflection of electrons on metal surfaces. Such a technology has been in prior use as an "e-beam tunnel" by the applicant.

Furthermore, EP 2 854 138 A1 discloses a surface decontamination device which has two lock devices and in which the handling of the objects to be decontaminated in the area of a radiation source is performed by two manipulator devices which can be moved in several dimensions.

In an alternative system, the outer packaging is conveyed through the decontamination chamber in a linear manner along a horizontal conveying path while being suspended by an annular shoulder, one lock chamber being disposed upstream and one lock chamber being disposed downstream of the decontamination chamber along the conveying path, the inlet and the outlet of each lock chamber being closable in an alternating manner by means of a door which can be displaced in a vertical manner, a free escape of radiation thus never being possible. By means of the known system, only outer packaging having the same dimensions can be processed without manual adjustments, because the outer packaging is transported while resting on its bottom until the decontamination chamber is reached and the outer packaging are then taken over by the suspension transport device in the decontamination chamber—the height distance between the bottom transport device which is disposed upstream of the decontamination chamber and the suspension transport device is predefined and would have to be adjusted in a time-consuming manual manner (if that is possible at all) in order to process outer packaging having other dimensions.

A system having a linear, aligned transport path is known from WO 2008/055375 A1, for example, said system also providing locks rotating about horizontal axes and having two parallel plates. The plates comprise recesses which are offset from one another in relation to the axis of rotation and which are cut out of material areas, an entry into the lock thus being possible in a first angular position and an exit from a lock being possible in a second angular position.

Similar locks which rotate about a vertical axis and which are provided with perpendicular shielding elements which extend radially to the axis are also known from US 2008/0193341 A1.

The aforementioned technologies haven proven their worth. However, the latter technology has the disadvantage that a transport of the outer packaging through the decontamination chamber during which the bottom of the outer packaging rests on a conveying device is problematic—firstly, because due to the extensive contact of the outer packaging with the conveying device, it is difficult to realize sufficient irradiation; additionally, the outer packaging often become jammed when they are being transported through the decontamination chamber. This is due to the relatively high flow velocities in the decontamination chamber which are caused by a positive pressure or the maintenance of the positive pressure which is normally provided on the side of the isolator.

SUMMARY OF THE INVENTION

Starting from the aforementioned state of the art, the object of the invention is to indicate an improved surface decontamination device, in particular realized as a transfer device for supplying outer packaging into an isolator, for decontaminating outer packaging containing pre-sterilized consumer goods, said device being suitable for decontaminating outer packaging having different dimensions, in particular a different vertical or height dimension, and said device reliably preventing radiation from escaping into the environment without the need for a labyrinth system while ensuring safe transport of the outer packaging through the decontamination chamber without jamming. Furthermore, the object is to indicate an improved system and an operating method.

Concerning the surface decontamination device, said object is attained by the features disclosed herein, i.e. concerning a generic device, by the fact that a lifting device for the, in particular translational, automatic vertical displacement of the outer packaging relative to the suspension transport device is disposed in the at least one lock chamber. The suspension transport device is preferably realized in such a manner that the respective bottom of the outer packaging is spaced apart from a bottom of the decontamination chamber and/or from decontamination chamber installations, the bottom thus levitating along the radiation source in the decontamination chamber.

Concerning the system, the object is attained by the features disclosed herein, i.e. in such a manner that an isolator which is preferably used for pharmaceutical applications and which is realized for processing the consumer goods unpacked from the outer packaging in the clean room, in particular in a manipulator chamber of the isolator, is to the decontamination device realized according to the idea of the invention. An unpacking chamber for the manual or automated unpacking (via a corresponding device) of the consumer goods from the outer packaging may be disposed between the isolator and the decontamination device. Alternatively, it is also possible within the scope of the invention to realize the isolator in such a manner that the consumer goods can be manually or automatically (via a corresponding device) unpacked from the decontaminated outer packaging in the isolator. In addition to the clean room, in particular the manipulator chamber for processing, in particular filling the consumer goods, the isolator comprises an air circulation generating chamber, in particular disposed upstream of the clean room, a plenum chamber being preferably disposed between the air circulation generating chamber and the clean room, said plenum chamber being separated from the clean room by a membrane for laminarizing an air flow. The isolator has preferably means for maintaining a positive pressure of the clean room.

Concerning the method, the object is attained by the features disclosed herein, i.e. concerning a generic method by the fact that the outer packaging is conveyed through the decontamination chamber by means of a suspension transport device while being suspended by its respective circumferential collar, in particular with the circumferential collar being clamped at the same time by means of clamping means, in particular between rollers and/or transport chains, and that the outer packaging is automatically displaced into the at least one lock chamber in a vertical, in particular translational, manner relative to the suspension transport device, in particular depending on the vertical extension, by means of a lifting device which is disposed in the lock chamber for the transfer onto the suspension transport device or, after the decontamination, for the transfer from the suspension transport device.

Advantageous embodiments of the invention are disclosed herein and in the dependent claims.

All combinations of at least two features disclosed in the description, the claims and/or the figures constitute part of the scope of the invention.

In order to avoid repetitions, disclosed features relating to the device are also seen as relating to the method and are thus also claimable therefor. In the same manner, disclosed features relating to the method are also seen as relating to the device and are thus also claimable therefor.

The idea of the invention is to provide a lock chamber according to the invention which is disposed upstream and/or downstream of the decontamination chamber along the conveying path and which has a lifting device for displacing the outer packaging in a vertical manner relative to a suspension transport device on the side of the decontamination chamber in order to compensate for a height difference between the edge of the outer packaging and the suspension transport device in an automatic (automated) manner by means of the (respective) lifting device in order to be able to transfer the outer packaging through the outlet of the lock chamber onto the suspension transport device at a transfer level if a lock chamber is provided upstream of the decontamination chamber in the conveying direction along the conveying path and/or, if such a lock chamber is disposed downstream of the decontamination chamber along the conveying path, to be able to transfer outer packaging at a transfer level from the suspension transport device through the inlet of the lock chamber and to deliver it to conveying means which are disposed downstream. By integrating a lifting device into such a lock chamber, it is possible to process outer packaging having different dimensions, in particular a different vertical dimension (distance from the lid film to the bottom of the outer packaging), without difficulties, because it is possible to compensate for a corresponding height difference or the different distances between the circumferential collar of outer packaging having different heights and the suspension transport device as early as inside the lock chamber. The invention generally also comprises a surface decontamination device in which a lock chamber having such a lifting device is alternatively disposed either upstream of the decontamination chamber only or downstream of the decontamination chamber only along the conveying path. In a particularly preferred embodiment, however, such a lock chamber having a lifting device is disposed both upstream and downstream of the decontamination chamber. The entire disclosure is to be understood in such a manner that it refers or can refer to both embodiments. The at least one lock chamber is preferably realized in such a manner that it can accommodate and adjust the height of one single piece of outer packaging after the other or a group of several pieces of outer packaging disposed one behind the other along the conveying path.

Due to the suspended transport of the outer packaging through the decontamination chamber, the bottom of the outer packaging can remain free and is therefore easily accessible for irradiation. Furthermore, jamming problems which can occur during a transport on the bottom of the outer packaging are avoided in a reliable manner, in particular since the surface pressure in the area of the circumferential collar, which has a smaller surface, is significantly greater than in the area of the bottom of the outer packaging, which has a larger surface. Moreover, as already mentioned, the suspension transport device can preferably be provided with clamping means in order to clamp the circumferential collar on at least one side during the transport, in particular between upper and lower transport rollers and/or between upper and lower transport chains and/or between at least one transport roller and at least one transport chain. In any event, suspended transport means that the weight force of the outer packaging is, at least partially, preferably largely, particularly preferably entirely, supported at the circumferential collar of the outer packaging during the transport through the decontamination chamber, a lid film closing the outer packaging being sealed at said circumferential collar according to a particularly preferred embodiment. However, the invention is not limited to such an embodiment of the outer packaging—the circumferential collar can also be realized inside the circumferential wall by an, in particular circumferential, annular shoulder, starting from which the circumferential wall extends both upwards towards an upper side of the outer packaging and downwards towards a bottom of the outer packaging. Said annular shoulder is preferably provided in addition to an upper circumferential collar which is disposed above the annular shoulder and at a distance thereto and to which a lid film is sealed. Alternatively, the suspended transport can be realized at the (upper) circumferential collar having a lid film or at an annular shoulder (circumferential collar) being disposed inside the circumferential wall of the outer packaging.

The at least one lock chamber is characterized by a closable inlet and by a closable outlet; i.e., the conveying path into the lock chamber and out of the lock chamber can be closed, in particular in a manner preventing the escape of radiation, by means of closing means, in the simplest manner by providing two doors which can be displaced in particular in a vertical manner, alternatively in a lateral manner, and which are preferably controlled in such a manner that the inlet and the outlet are opened in an alternating manner only, i.e., not at the same time, in operation, in order to reliably prevent radiation from escaping. If a lock chamber is provided upstream of the decontamination chamber along the conveying path, the inlet of the lock chamber is used in order to pass outer packaging or to take over outer packaging from a transport device which is disposed upstream and which preferably transports the outer packaging with the outer packaging resting on its bottom. After displacing the outer packaging in a vertical manner, said outer packaging passes through the outlet of such a lock chamber into the adjacent decontamination chamber. If a lock chamber is provided downstream of the decontamination chamber along the conveying path, the sterilized outer packaging travels from the decontamination chamber through the inlet of the lock chamber into the lock chamber and is conveyed through the outlet, in particular after a vertical displacement, preferably upwards, towards an isolator, preferably again with the outer packaging resting on the bottom of the outer packaging. So a change of the transport system is particularly preferably realized in such a manner that, preferably, the outer packaging is conveyed into a lock chamber which is disposed upstream of the decontamination chamber while resting on the bottom of the outer packaging and that the outer packaging is then conveyed in a suspended manner inside the lock chamber. Additionally or alternatively, it is preferred if decontaminated outer packaging returns to resting on its bottom in a preferably provided lock chamber which is disposed downstream of the decontamination chamber and if the outer packaging is or can be conveyed on towards the isolator while resting on its bottom.

Overall, the surface decontamination device according to the invention is characterized in that the outer packaging can be transported in an essentially linear manner along the conveying path except for the small height offset in the at least one lock chamber, i.e., in such a manner that no labyrinth requiring a lot of space has to be realized. In other words, the at least one lock chamber and the decontamination chamber, preferably lock chambers disposed on two sides of the decontamination chamber facing away from one another, are disposed in such a manner that an imaginary horizontal line runs through the inlet and the outlet of the at least one lock chamber, preferably of both lock chambers, and through the decontamination chamber. Furthermore, conveying problems in the counter air flow which is preferably provided in the decontamination chamber are avoided by means of the suspended transport, while ensuring that outer packaging having different height dimensions can be processed or transferred towards the isolator without major rearrangements of the machinery by providing the lifting device in the at least one lock chamber.

In a particularly preferred embodiment of the device according to the invention and/or of the operating method according to the invention, the time for opening and/or closing the inlet of the lock chamber or the outlet of the lock chamber in order to vertically displace the at least one, preferably solely one, outer packaging located in the lock chamber at a given time relative to the suspension transport device is used for a delivery or transfer of the outer packaging onto or from the suspension transport device. In other words, the vertical displacement is at least partially realized, i.e., at least starts, before the inlet of the lock chamber is entirely closed and/or the outlet towards the decontamination chamber is entirely opened. The lifting movement is particularly preferably completed before the outlet is entirely opened. Concerning a lock chamber which is disposed downstream of the decontamination chamber, the vertical displacement of the outer packaging in the vertical direction is preferably at least temporarily realized, i.e., the lifting process at least starts, before the inlet (connection to the decontamination chamber) is entirely closed and/or the outlet is entirely opened. The lifting movement is particularly preferably completed before the outlet is entirely opened. For the realization according to the device, the control means control the corresponding lifting device and the closing means in a corresponding manner in order to realize an overlap in time.

According to the invention, the closing means comprise an, in particular metallic, circumferential wall, preferably on the entire circumference, which can be rotated about an axis of rotation and which has at least solely one opening which can be displaced into the conveying path and which is realized in such a manner that the inlet and the outlet of the lock chamber can be opened solely in an alternating manner. In other words, a circumferential wall is preferably to be disposed so as to be rotatable in order to realize an inlet and an outlet which can be opened solely in an alternating manner, said circumferential wall being preferably circumferentially closed except for the at least one passage opening for transporting the outer packaging through it and said circumferentially wall at least partially surrounding the lifting device. For realizing the alternating opening of the inlet and the outlet of the lock chamber according to the invention, the circumferential wall has a single passage opening which realizes either the inlet or the outlet depending on the rotational position. The rotatable circumferential wall is preferably disposed inside an outer protective wall which is in particular made of metal and which leaves space for the movement path of the outer packaging into and out of the lock chamber and which adjoins the outlet, in particular on two circumferential sides, in order to ensure that no radiation can escape when the circumferential wall is pivoted or rotated.

With respect to the specific embodiment of the lifting device, different possibilities are available. A linear drive is preferably realized, for example by providing a pneumatic or hydraulic piston-cylinder unit, alternative linear drives, for example in the form of an electromotive spindle drive or a toothed belt drive being also realizable. Preferably, the lifting device is essentially a lifting adjustment device, i.e., a lifting device which has a comparatively small lift compared to the labyrinth solution of the state of the art, because the outer packaging must be conveyable through the outlet or inlet (depending on the disposition of the lock chamber) towards or from the decontamination chamber when they are lifted. The maximum lift is preferably smaller than the vertical dimension of an outer packaging which can be handled or decontaminated by means of the surface decontamination device at maximum. The lifting device can also comprise a slide which can be displaced in a vertical manner, in particular by means of belt drive, and which is preferably fixed to the belt, the belt being driven by a drive shaft and guided around a deviating shaft on the opposite side.

The lifting device preferably comprises a conveying device of the conveying means by means of which the outer packaging (depending on whether the lock chamber is disposed upstream or downstream of the decontamination chamber) can be conveyed into or out of the decontamination chamber. The conveying device is preferably integrated into a lifting platform of the lifting device and is thus displaced in the vertical direction together with the outer packaging. The conveying device preferably comprises a conveyor belt, conveyor rollers or a conveyor strap, the packaging bottom of the outer packaging resting on the conveying device, which means that the conveying principle necessarily changes, namely from a delivering transport, during which the packaging bottom of the outer packaging is supported by a conveying device, and the suspended transport in the decontamination chamber and again a transport on the bottom of the outer packaging which preferably takes place downstream of the decontamination chamber. In a particularly preferred embodiment, the conveyor belt, the conveyor rollers or the conveyor strap is/are driven, in particular in an electromotive manner, through a vertical hollow shaft of the lifting device via a corresponding angle gear.

According to an embodiment of the device according to the invention and of the method according to the invention, the displacement path of the at least one lifting device and/or the radiation intensity of the at least one radiation source and/or the conveying speed of the conveying means at which the outer packaging can be or is conveyed through the decontamination chamber can be or are varied depending on the type of outer packaging. In other words, the control of the lifting device and/or of the radiation source, in particular with respect to its intensity, and/or the control of the conveying means, in particular with respect to its conveying speed, is realized depending on different sequential programs for specific types of outer packaging, each type of outer packaging to be processed being either manually defined, in particular by selecting a corresponding program for a specific type of outer packaging, and/or automatically defined, i.e., by sensing or identifying a respective type of outer packaging, for example by sensing a packaging size or an outer packaging size or a parameter depending on the size of the outer packaging and/or by reading out a code provided in and/or on the packaging, one of several sequential programs of the control device being automatically selected depending on the identified type of outer packaging. It is also conceivable to provide sequential program parameters directly in an outer packaging code, such as a QR code or a barcode.

If a manual selection of the sequential program is realized, the device realized according to the idea of the invention preferably comprises corresponding input means for a user. If the sequential program is automatically selected and/or a selection of the program is parametrized by means of a parameter provided in a code, the device preferably comprises sensor means for the automated detection of different packaging types, for example by identifying a packaging geometry and/or by reading out an outer packaging code.

BRIEF DESCRIPTION OF THE DRAWINGS

Further advantages, features and details of the invention can be derived from the following description of a preferred exemplary embodiment and from the drawing.

In the drawing,

FIG. 1 is a perspective, longitudinal section view of a preferred exemplary embodiment of a surface decontamination device realized according to the idea of the invention for realizing an operating method according to the invention.

DETAILED DESCRIPTION

In FIG. 1, a surface decontamination device 1 realized as a transfer device is shown, an isolator known per se (not shown) being disposed downstream of said surface decontamination device 1 in a conveying direction F within the scope of a system according to the invention. Surface decontamination device 1 is used for decontaminating outer packaging 2 having a circumferential collar 3, in particular on the entire circumference, a lid film 4 being sealed thereon. Outer packaging 2 (only one of which is shown in an exemplary manner in FIG. 1) contains consumer goods, such as prefilled syringes.

In the center or as a core component, device 1 comprises a decontamination chamber 5, outer packaging 2 being conveyed one after the other through said decontamination chamber 5 and being exposed to radiation, electron radiation in the present case, therein. To this end, an (electron) radiation source 6 is assigned to decontamination chamber 5 in a manner known per se. The outer packaging 2 is transported through decontamination chamber 5 while being suspended by circumferential collar 3, circumferential collar 3 being clamped by a suspension transport device 7 (partially shown) on two opposite sides, for example between conveyor rollers and/or conveyor chains which are disposed above and below circumferential collar 3.

A gap which can be bridged or passed over is preferably provided between units of suspension transport device 7 inside decontamination chamber 5 in order to make the clamped areas accessible for irradiation.

A first lock chamber 8 is disposed upstream of decontamination chamber 5 in conveying direction F, said lock chamber 8 having a rotatable first circumferential wall 9 made of metal in the shown exemplary embodiment, circumferential wall 9 having a single, radial first passage opening 10 in the specific exemplary embodiment, said first passage opening 10 realizing an inlet in the shown rotational position in order to be able to supply an outer packaging 2. First lock chamber 8 is closed on the outlet side and therefore encapsulated in relation to decontamination chamber 5. By rotating first circumferential wall 9 by 180°, the passage to decontamination chamber 5 is opened, first passage opening 10 realizing the outlet of first lock chamber 8, an outer packaging 2 thus being transferable through the outlet into decontamination chamber 5, first lock chamber 8 being closed on the inlet side at this time via first circumferential wall 9. A first lifting device 11 having a lifting platform 12 is located inside first lock chamber 8, a first conveying device 13, in the present case in the form of a belt drive, being located thereon in order to be able to take over outer packaging 2 from conveying means in an area downstream of first lock chamber 8 in conveying direction F and to transfer outer packaging 2 onto suspension transport device 7 of decontamination chamber 5 after a vertical displacement in an upward direction. The vertical displacement is preferably at least temporarily realized before the lock chamber is closed again on the outlet side by rotating first circumferential wall 9.

A second lock chamber 14 which has a second lifting device 15 and a second conveying device 16 disposed thereon and which is realized in a manner essentially identical to first lock chamber 8 is disposed downstream of decontamination chamber 5 in order to be able to take over outer packaging 2 from suspension transport device 7 and to vertically displace outer packaging 2 in a downward direction in order to be able to transfer said outer packaging 2 onto conveying means disposed downstream for further transport into the isolator. Second lock chamber 14 comprises or is limited in the radial direction by a second rotatable circumferential wall 17 having a single second passage opening 18 which realizes an inlet, i.e., a connection, to decontamination chamber 5 or an outlet as a connection towards the isolator in an alternating or alternative manner. The vertical displacement of second lifting device 15, in the present case in a downward direction, is preferably at least temporarily realized while second circumferential wall 17 is being rotated, i.e., the vertical displacement at least starts before the outlet is entirely opened towards the isolator.

An air outlet 20 is located in an area above first lock chamber 8 in order to discharge the air flow coming from the direction of the isolator in an area upstream of decontamination chamber 5 in conveying direction F.

FIG. 1 also shows that both lock chambers are connected to decontamination chamber 5 in a permanently air-conducting manner regardless of the opening state of the inlet and the outlet in order to ensure air passage from the isolator against conveying direction F.

Control means (controller, control device) are assigned to the conveying means, in particular to suspension transport device 7, and to both lifting devices 11, 12 and to radiation source 6, said control means controlling said functional units as explained in the general description depending on a type of outer packaging which is manually defined or automatically detected, i.e., in such a manner that the correct lifting path of the lifting devices and/or a corresponding radiation intensity of radiation source 6 and/or a conveying speed of suspension transport device 7 is/are defined.

REFERENCE SIGNS 1 device
2 outer packaging
3 circumferential collar
4 lid film
5 decontamination chamber
6 radiation source
7 suspension transport device
8 first lock chamber
9 first circumferential wall
10 first passage opening
11 first lifting device
12 first lifting platform
13 first conveying device
14 second lock chamber
15 second lifting device
16 second conveying device
17 second circumferential wall
18 second passage opening
20 air outlet
F conveying direction

The invention claimed is:

1. A surface decontamination device (1) for decontaminating outer packaging (2) which contains pre-sterilized consumer goods, and which has a circumferential collar (3) prior to transfer into an isolator, said surface decontamination device (1) comprising conveying means for conveying the outer packaging (2) in a conveying direction (F) along a conveying path from an inlet side of the surface decontamination device to an outlet side of the surface decontamination device (1), the conveying path passing through a decontamination chamber (5) which is disposed between the inlet side and the outlet side and to which a radiation source (6), is assigned for irradiating the outer packaging (2) which can be conveyed through the decontamination chamber (5), and through at least one lock chamber (8) which is disposed between the inlet side and the outlet side and which is adjacent to the decontamination chamber (5) and which has an inlet and an outlet, said inlet and outlet being able to be opened and closed by closing means, the conveying means comprising a suspension transport device (7) disposed in the decontamination chamber (5) for suspended transport of the outer packaging (2) by its circumferential collar (3), wherein the closing means comprise a circumferential wall (9, 17) which can be rotated about an axis of rotation and which has solely one opening which can be displaced into the conveying path for conveying the outer packaging (2) through said circumferential wall (9, 17) which is realized in such a manner that the inlet and the outlet can be opened solely in an alternating manner, a lifting device (11, 15) for an automatic, vertical displacement of the outer packaging (2) relative to the suspension transport device (7) being disposed in the at least one lock chamber (8, 14).

2. The surface decontamination device according to claim 1, wherein the lifting device (11, 15) has a linear drive for the automatic, vertical displacement of a lifting platform (12).

3. The surface decontamination device according to claim 2, wherein the linear drive is a piston-cylinder unit and/or a toothed belt drive.

4. The surface decontamination device according to claim 2, wherein a conveying device of the conveying means is integrated into the lifting device (11, 15) for conveying the outer packaging (2) towards the outlet of the at least one lock chamber (8).

5. The surface decontamination device according to claim 4, wherein the conveying device comprises at least one conveyer roller, a conveyor belt, or a conveyor strap, wherein the conveying device conveys the outer package in a horizontal manner and is drivable through a vertical hollow shaft.

6. The surface decontamination device according to claim 1, further comprising a control device which is realized for controlling the lifting device (11, 15) and/or the radiation source (6) and/or the conveying means depending on different sequential programs for specific types of outer packaging which can be manually or automatically selected.

7. The surface decontamination device according to claim 6, wherein the control device controls the lifting device (11, 15) and/or the radiation source (6) and/or the conveying means depending on specific dimensions of outer packaging.

8. The surface decontamination device according to claim 6, further comprising input means for the manual selection of a sequential program and/or a specification of the type of outer packaging and/or a specification of the dimension of the outer packaging, by a user and/or sensor means for an automated detection of different types of outer packaging.

9. The surface decontamination device according to claim 8, wherein the input means is for the the specification of height of the outer packaging, or wherein the sensor means is for an automated detection of different dimensions of the outer packaging.

10. The surface decontamination device according to claim 1, wherein the at least one lock chamber (8) is disposed upstream of the decontamination chamber (5) in the conveying direction (F), in such a manner that the outer packaging (2) can be conveyed from the outlet of the at least one lock chamber (8) into the decontamination chamber (5) and/or wherein the at least one lock chamber (14) is disposed downstream of the decontamination chamber (5) in the conveying direction (F), in such a manner that the outer packaging (2) can be conveyed from the decontamination chamber (5) into the inlet of the at least one lock chamber (14).

11. The surface decontamination device according to claim 1, wherein the at least one lock chamber (8, 14) is disposed in such a manner that an imaginary horizontal line runs through the inlet and the outlet of the at least one lock chamber (8, 14) and through the decontamination chamber (5).

12. The surface decontamination device according to claim 11, wherein the at least one lock chamber (8, 14) is disposed in such a manner that the imaginary horizontal line runs through the inlet and the outlet of two lock chambers.

13. The surface decontamination device according to claim 1, wherein the pre-sterilized consumer goods are prefilled syringes, and wherein the radiation source (6) is an electron beam source.

14. A system comprising a surface decontamination device (1) according to claim 1, and an isolator which is disposed downstream of said surface decontamination device (1) for processing the pre-sterilized consumer goods unpacked from the outer packaging (2) in a clean room.

15. The system according to claim 4, wherein the isolator is a pharmaceutical isolator, and wherein the clean room is a manipulator chamber of the isolator.

16. A method for operating a surface decontamination device (1) according to claim 1, outer packaging (2) having a circumferential collar (3) and being closed on the circumferential collar (3) by means of a film and containing pre-sterilized consumer goods disposed therein being conveyed from the inlet side of the surface decontamination device (1) to the outlet side of the surface decontamination device (1) in the conveying direction (F) along the conveying path prior to transfer into an isolator and being exposed to radiation, on the conveying path in the decontamination chamber (5), the outer packaging (2) being conveyed through the at least one lock chamber (8, 14) having the inlet and the outlet and being disposed upstream and/or downstream of the decontamination chamber (5), the inlet and the outlet of the at least one lock chamber (8, 14) being able to be opened and closed by the closing means in order to prevent radiation from escaping, the outer packaging (2) being conveyed through the decontamination chamber (5) while being suspended by its respective circumferential collar (3) by the suspension transport device (7), with the circumferential collar (3) being clamped, wherein the outer packaging (2) is automatically displaced in a vertical manner relative to the suspension transport device (7) in the at least one lock chamber (8, 14), depending on its vertical extension, for the transfer onto the suspension transport device (7) or, after the decontamination chamber (5), for the transfer from the suspension transport device (7) by means of the lifting device (11, 15) disposed in the at least one lock chamber (8, 14), the closing means comprising the circumferential wall (9, 17) which can be rotated about an axis of rotation and which has solely one opening which can be displaced into the conveying path for conveying the outer packaging (2) through said circumferential wall (9, 17) which opens the inlet and the outlet solely in an alternating manner.

17. The method according to claim 16, wherein the outer packaging (2) is at least temporarily displaced within the at least one lock chamber (8, 14) in a vertical manner by means of the lifting device (11, 15) when the inlet and/or the outlet is/are being opened and/or closed.

18. The method according to claim 17, wherein the outer packaging (2) is entirely displaced within the at least one lock chamber (8, 14) in a vertical manner by means of the lifting device (11, 15) when the inlet and/or the outlet is/are being operated.

* * * * *